(12) United States Patent
Liphardt et al.

(10) Patent No.: US 7,738,105 B1
(45) Date of Patent: *Jun. 15, 2010

(54) SYSTEM AND METHOD OF APPLYING HORIZONTALLY ORIENTED ARC-LAMPS IN ELLIPSOMETER OR THE LIKE SYSTEMS

(76) Inventors: Martin M. Liphardt, 5901 Brandford Pl., Lincoln, NE (US) 68512; Ping He, 2628 Wilderness Ridge Cir., Lincoln, NE (US) 68512; James D. Welch, 10328 Pinehurst Ave., Omaha, NE (US) 68124

(*) Notice: Subject to any disclaimer, the term of this patent is extended or adjusted under 35 U.S.C. 154(b) by 579 days.

This patent is subject to a terminal disclaimer.

(21) Appl. No.: 11/636,761

(22) Filed: Dec. 11, 2006

Related U.S. Application Data

(63) Continuation-in-part of application No. 11/084,827, filed on Mar. 21, 2005, now Pat. No. 7,301,631, application No. 11/636,761, and a continuation-in-part of application No. 11/105,852, filed on Apr. 14, 2005, now Pat. No. 7,277,171.

(60) Provisional application No. 60/611,173, filed on Sep. 17, 2004, provisional application No. 60/564,747, filed on Apr. 23, 2004, provisional application No. 60/749,768, filed on Dec. 13, 2005.

(51) Int. Cl.
*G01N 21/55* (2006.01)
(52) U.S. Cl. ..................................... 356/445
(58) Field of Classification Search .......... 356/445–448
See application file for complete search history.

(56) References Cited

U.S. PATENT DOCUMENTS

| | | | |
|---|---|---|---|
| 3,874,797 A | 4/1975 | Kasai | 356/369 |
| 4,210,401 A * | 7/1980 | Batten | 356/369 |
| 4,332,476 A | 6/1982 | Stenberg et al. | 356/369 |
| 4,647,207 A | 3/1987 | Bjork et al. | 356/369 |
| 4,681,450 A | 7/1987 | Azzam | 356/367 |
| 4,790,659 A | 12/1988 | Erman et al. | 356/369 |
| 5,229,833 A | 7/1993 | Stewart | 356/364 |
| 5,343,293 A | 8/1994 | Berger et al. | 356/369 |
| 5,764,365 A | 6/1998 | Finarov | 356/630 |
| 5,963,327 A | 10/1999 | He et al. | 356/369 |
| 5,969,818 A | 10/1999 | Johs et al. | 356/369 |
| 6,414,302 B1 * | 7/2002 | Freeouf | 250/225 |
| RE38,153 E | 6/2003 | Finarov | 356/630 |
| 6,714,301 B2 | 3/2004 | Otsuki et al. | 356/369 |
| 6,753,962 B2 | 6/2004 | Opsal et al. | 356/369 |
| 6,795,184 B1 | 9/2004 | Herzinger et al. | 356/369 |
| 7,489,400 B1 * | 2/2009 | He et al. | 356/369 |
| 2002/0159063 A1 | 10/2002 | Kanzaki | |
| 2004/0085538 A1 | 5/2004 | Hovinen et al. | |
| 2006/0126079 A1 * | 6/2006 | Bareket et al. | 356/625 |

* cited by examiner

*Primary Examiner*—Michael P Stafira
(74) *Attorney, Agent, or Firm*—James D. Welch

(57) ABSTRACT

Control of the angle-of-incidence of a beam of electromagnetic radiation provided by a horizontally oriented arc-lamp in ellipsometer, polarimeter, spectrophotometer, reflectometer, or the like systems.

3 Claims, 5 Drawing Sheets

SYSTEM AND METHOD OF APPLYING HORIZONTALLY ORIENTED ARC-LAMPS IN ELLIPSOMETER OR THE LIKE SYSTEMS

This application is a CIP of application Ser. No. 11/084,827 Filed Mar. 21, 2005 now U.S. Pat. No. 7,301,631 and therevia Claims Benefit of Provisional Application Ser. No. 60/611,173 Filed Sep. 17, 2004, and is a CIP of application Ser. No. 11/105,852 Filed Apr. 14, 2005 now U.S. Pat. No. 7,277,171 and therevia Claims Benefit of Provisional Application Ser. No. 60/564,747 Filed Apr. 23, 2004; and the Application directly Claims Benefit of Provisional Application Ser. No. 60/749,768 Filed Dec. 13, 2005.

TECHNICAL FIELD

The present invention relates to sources of electromagnetic radiation and more particularly to horizontally oriented arc-lamps applied in spectrophotometer, reflectometer, ellipsometer, polarimeter, Mueller matrix measuring, or the like systems.

BACKGROUND

It is known to apply arc-lamps in spectrophotometer, reflectometer, ellipsometer, polarimeter or the like systems which direct beams of electromagnetic radiation therefrom to samples at normal or oblique angles-of-incidence. It is further known that arc-lamps generally present with an elongated dimension. Manufacturer recommendation is that arc-lamps be mounted so that their elongated dimension is oriented vertically. The problem this presents in application to spectrophotometer, reflectometer, ellipsometer, polarimeter or the like systems is that as an arc-lamp ages, the focal point from which a beam of electromagnetic radiation therefrom originates moves. This effectively changes the angle-of-incidence of the beam to a sample surface. As said angle-of-incidence must be known to enable valid analysis of data corresponding to reflected or transmitted electromagnetic radiation from or through said sample, it can be appreciated that where arc-lamps are mounted with their elongated dimension oriented vertically in spectrophotometer, reflectometer, ellipsometer, polarimeter or the like systems, problems are present.

One solution is to use a sequence of mirrors to rotate the locus of the elongated dimension of an arc-lamp 90 degrees. Then as the origin of the beam changes, the angle-of-incidence does not change. Rather a the beam impinges on a sample surface at a laterally slightly different point. Another approach is to ignore manufacturer recommendations and mount the arc-lamp so that elongated dimension thereof projects horizontally. However, when this is done it is found that the upper inner surface of the arc-lamp becomes progressively less transparent because of sputtered depositions thereon. The lower inner surface of the horizontally oriented arc-lamp, however, remains relatively unaffected.

The following patents all describe ellipsometer or the like systems which comprise a plurality of reflective means and/or means for directing beams:

U.S. Pat. No. 5,969,818 to Johs et al.;
U.S. Pat. No. 5,764,365 to Finarov;
U.S. Pat. No. 5,343,293 Berger et al.;
U.S. Pat. No. 4,647,207 to Bjork et al.;
U.S. Pat. No. 3,874,797 to Kasai;
U.S. Pat. RE38,253 to Finarov;
U.S. Pat. No. 6,714,301 to Otsuki et al.;
U.S. Pat. No. 6,753,962 to Opsal et al.;
U.S. Pat. No. 5,229,833 to Stewart;
U.S. Pat. No. 4,790,659 to Erman et al.;
U.S. Pat. No. 4,210,401 to Batten;
U.S. Pat. No. 5,963,327 to He et al.;
U.S. Pat. No. 6,795,184 to Herzinger at al.
U.S. Pat. No. 4,681,450 to Azzam;
U.S. Pat. No. 4,332,476 to Stenberg et al.
Published Application No. US 2004/0085538 A1 by Hovinen et al.;
Published Application No. US 2002/0159063 A1 by Kanzaki.

Even in view of the prior art need remains for improved means of providing beams for horizontally oriented arc-lamps in spectrophotometer, reflectometer, ellipsometer, polarimeter Mueller Matrix measuring, or the like system.

DISCLOSURE OF THE INVENTION

The present invention is based in a common need to be able to easily provide more than one angle-of-incidence of a beam of electromagnetic radiation to a sample surface, when obtaining data using a spectrophotometer, reflectometer, ellipsometer, polarimeter or the like systems. And the present invention is further based in the fact that where the source of the beam of electromagnetic radiation is an arc-lamp with an elongated dimension thereof oriented horizontally, it is necessary to take precautions to assure that said beam exist a relatively clear lower inner surface of the horizontally oriented arc-lamp, which remains relatively unaffected over time of usage.

The present invention provides that electromagnetic radiation be obtained from the lower inner surface of a horizontally oriented arc-lamp, and that a reflective means be applied to direct said beam to a sample surface. When the angle-of-incidence of the beam with respect to said sample surface is to be changed, the vertical height of the reflective means is changed simultaneously with rotating it to change the angle said beam reflects from said reflective means. This results in a beam of electromagnetic radiation always exiting the lower inner surface of the horizontally oriented arc-lamp, and progressing to reflect from said reflective means and impinge on the surface of the sample at substantially the same point thereon, no matter what angle-of-incidence is chosen. A variation on the disclosed invention provides that the horizontally oriented arc-lamp be changed simultaneously with rotating the reflective means to change the angle said beam reflects from said reflective means.

In particular the just described system is beneficially applied in ellipsometer and polarimeter systems comprising:

a source of a beam of electromagnetic radiation comprising:
an arc-lamp which presents with an elongated dimension, said arc-lamp being oriented such that its elongated dimension projects substantially horizontally, said system further comprising means for controlling the vertical location thereof, said system further comprising a reflective means and means for controlling the vertical location thereof and for rotating said reflective means; such that in use a beam of electromagnetic beam is produced by said arc-lamp and directed out the lower surface thereof onto said reflective means, which reflectively directs it at a first angle-of-incidence onto a spot on a sample surface; and such that when the vertical location of said reflective means is changed and said reflective means is rotated, said beam produced by said arc-lamp and directed out the lower surface thereof onto said reflective means is directed to the same spot on said sample surface at a second angle-of-incidence;

a sample;
a polarizer between said source of a beam of electromagnetic radiation and said sample;
detector after said sample; and
an analyzer between said sample and said detector.

Said system can further comprises at least one compensator between said source of a beam of electromagnetic radiation comprising and said detector, and the vertical location of said arc-lamp can also changed when the vertical location of said reflective means is changed.

A mechanical system for setting the angle of incidence of a beam of electromagnetic radiation comprises, as viewed in elevation, first and second arms pivotally interconnected to one another at an upper aspect thereof by a first pivot means, said first and second arms projecting downward and to the left and right of said first pivot means. Distal ends of said first and second arms are pivotally affixed to third and forth arms, said third and forth arms being pivotally interconnected to one another at a lower aspect thereof and said third and forth arms being projected upward and to the left and right of said pivotal interconnection at said lower aspect thereof, respectively. There are at least two pivotally affixed substantially downward projecting arms attached to each of said third and forth arms, distal ends of which are pivotally affixed to fifth and sixth arms which are not interconnected to one another, but project upward to the left and right, respectively. Affixed to one of said fifth and sixth arms is a source of a beam of electromagnetic radiation, and to the other of said sixth and fifth arms a detector of said beam of electromagnetic radiation is affixed. There is further a sample located such that a beam of electromagnetic radiation produced by said source of a beam of electromagnetic radiation reflects from an upper surface of said sample and enters said detector of said beam of electromagnetic radiation. In use when the first pivot means at which said first and second arms are interconnected is caused to be vertically raised or lowered, the angle of incidence at which the beam of electric radiation approaches said sample surface is changed, but the location at which it interacts with said sample surface remains substantially unchanged.

It is noted that the present invention can be applied in wavelength ranges, such as:
VUV;
UV;
Visible;
Infrared;
Far Infrared;
Radio Wave.

The present invention will be better understood by a reading of the Detailed Description Section of this Specification, in combination with reference to the Drawings.

BRIEF DESCRIPTION OF THE DRAWINGS

FIG. 3b shows a variation on FIG. 3a.

DETAILED DESCRIPTION

Figure 1:
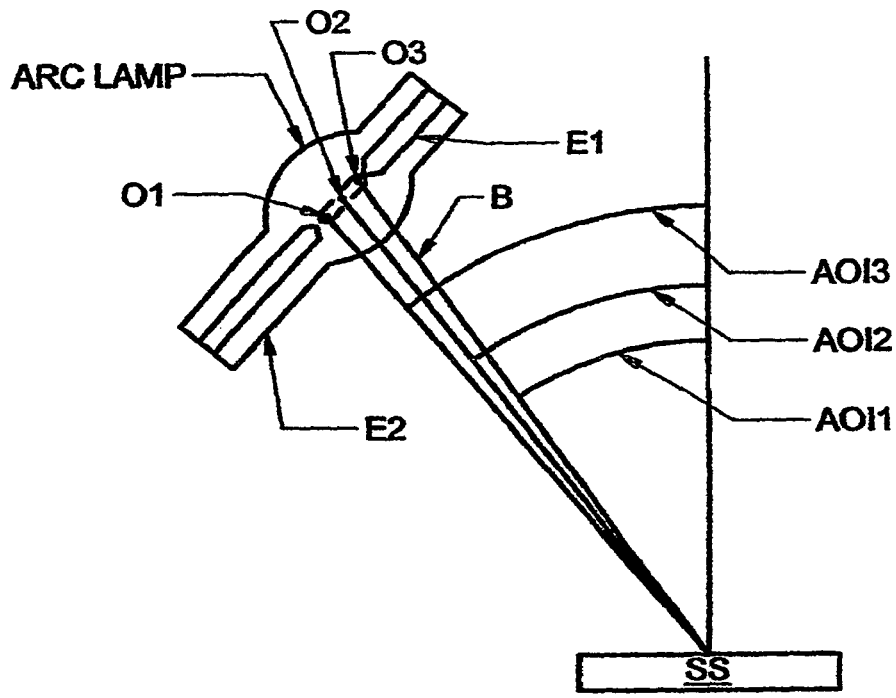
FIG. 1 shows how the effective source point (eg. O1, O2, O3), of a substantially vertically oriented arc-lamp can change over time

FIG. 1 shows how the effective source point (eg. O1, O2, O3), of a substantially vertically oriented arc-lamp can change over time of use, and how that change can affect the angle-of-incidence the Beam (E) from said arc-lamp to the surface of the sample changes in response, (eg. AOI1, AOI2, AOI3).

Figure 2A:
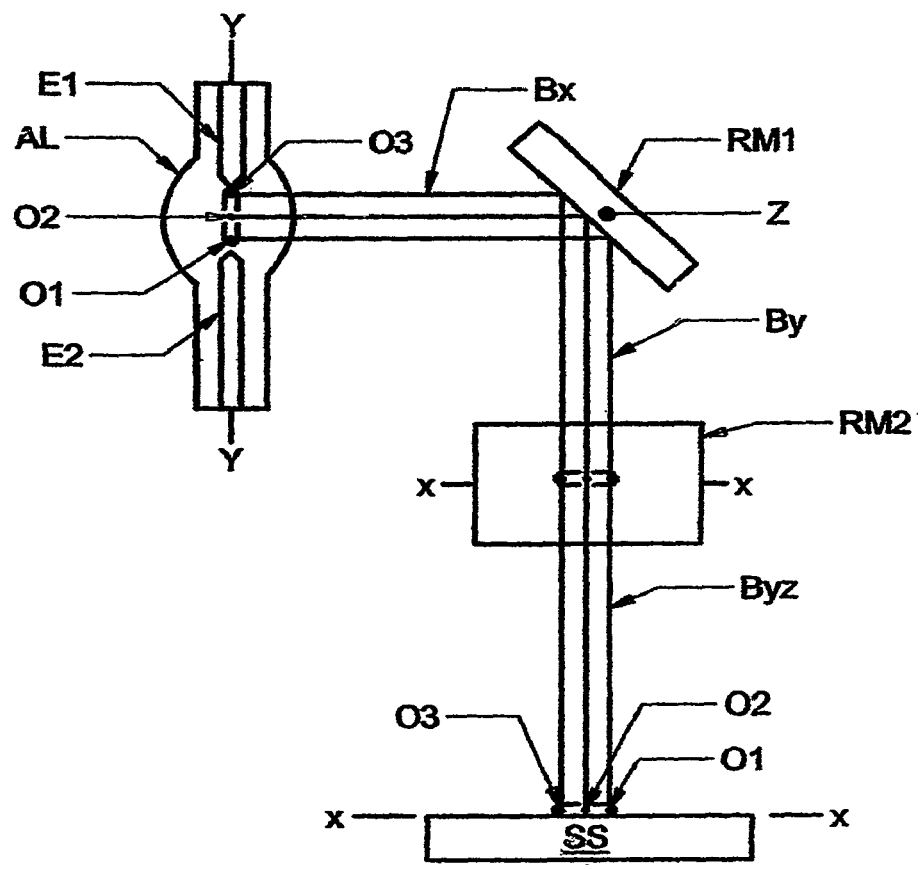
FIGS. 2a and 2b show a system comprising a double mirror (RM1) (RM2) arrangement to rotate the image of a vertically oriented arc-lamp (AL) into a horizontally oriented plane.
Figure 2B:
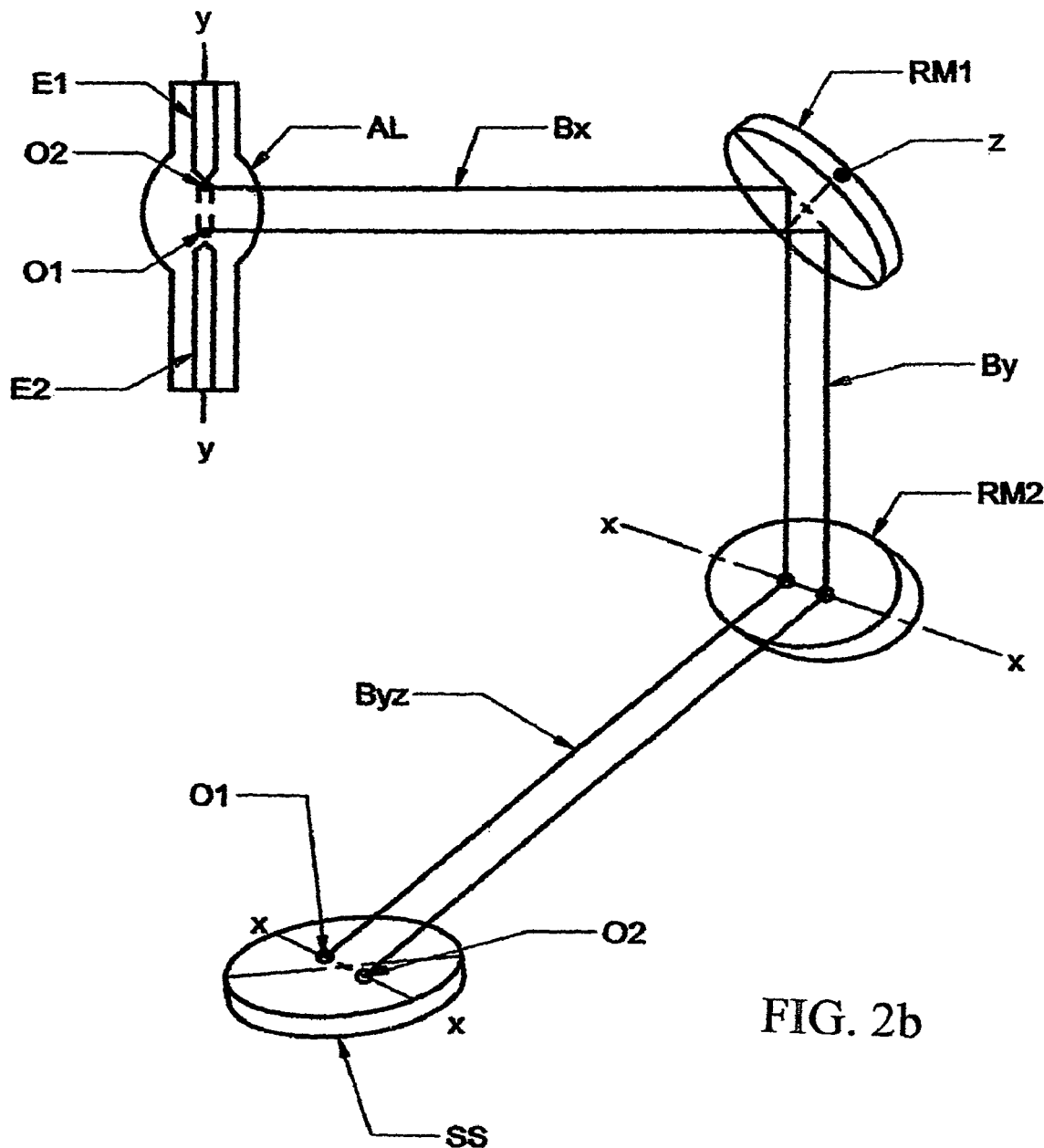

FIGS. 2a and 2b show a system comprising a double mirror (RM1) (RM2) arrangement to rotate the image of a vertically oriented arc-lamp (AL) into a horizontally oriented plane. This is Claimed in patent application Ser. No. 11/084,827.

Figure 3A:
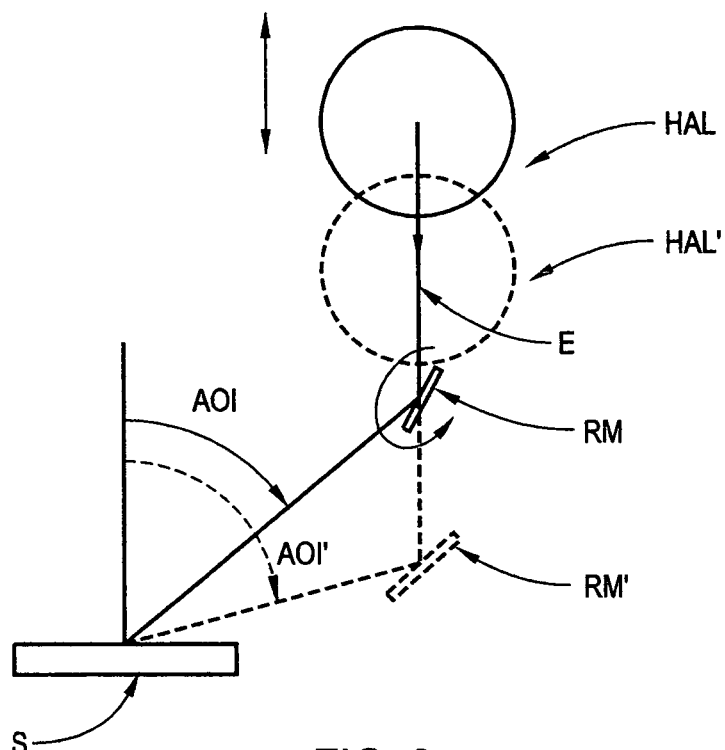
FIG. 3a shows the present invention approach of using a horizontally oriented arc-lamp (HAL) from which a beam (E) always exists the lower surface thereof and reflects from a reflective means (RM).
Figure 3B:
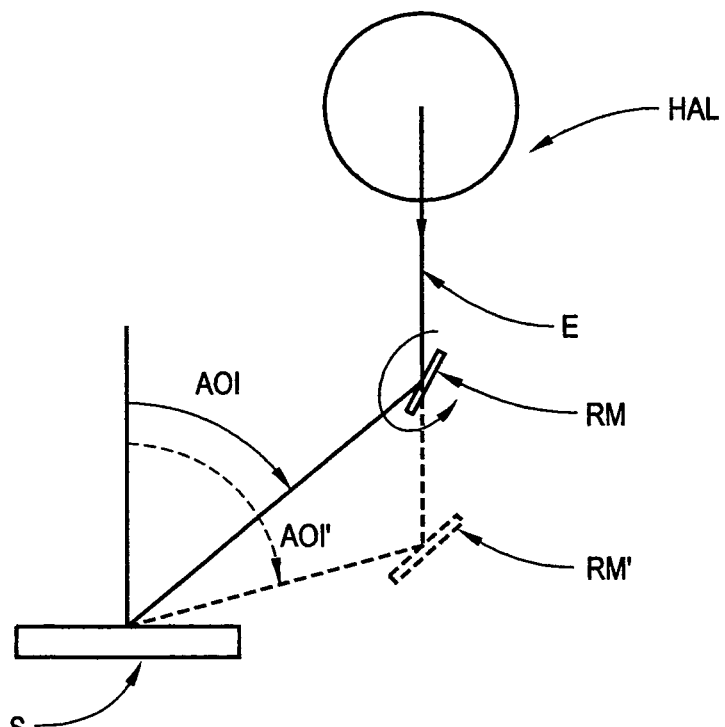

FIG. 3a shows the present invention approach of using a horizontally oriented arc-lamp (HAL) from which a beam (E) always exists the lower surface thereof and reflects from a reflective means (RM). The angle-of-incidence (AOI) of said beam to the sample surface is determined by the angle of said reflective means (RM). Note that if the arc-lamp (HAL') is moved downward and the reflective means (RM') is also moved down and rotated as shown, the angle-of-incidence (AOI') is changed, but that the beam (E) still exits the lower portion of the horizontally oriented arc-lamp. FIG. 3b shows a variation on FIG. 3a, wherein only the reflective means (RM) is moved and rotated to position (RM'), and the arc-lamp (HAL) remains stationary.

Figure 4:
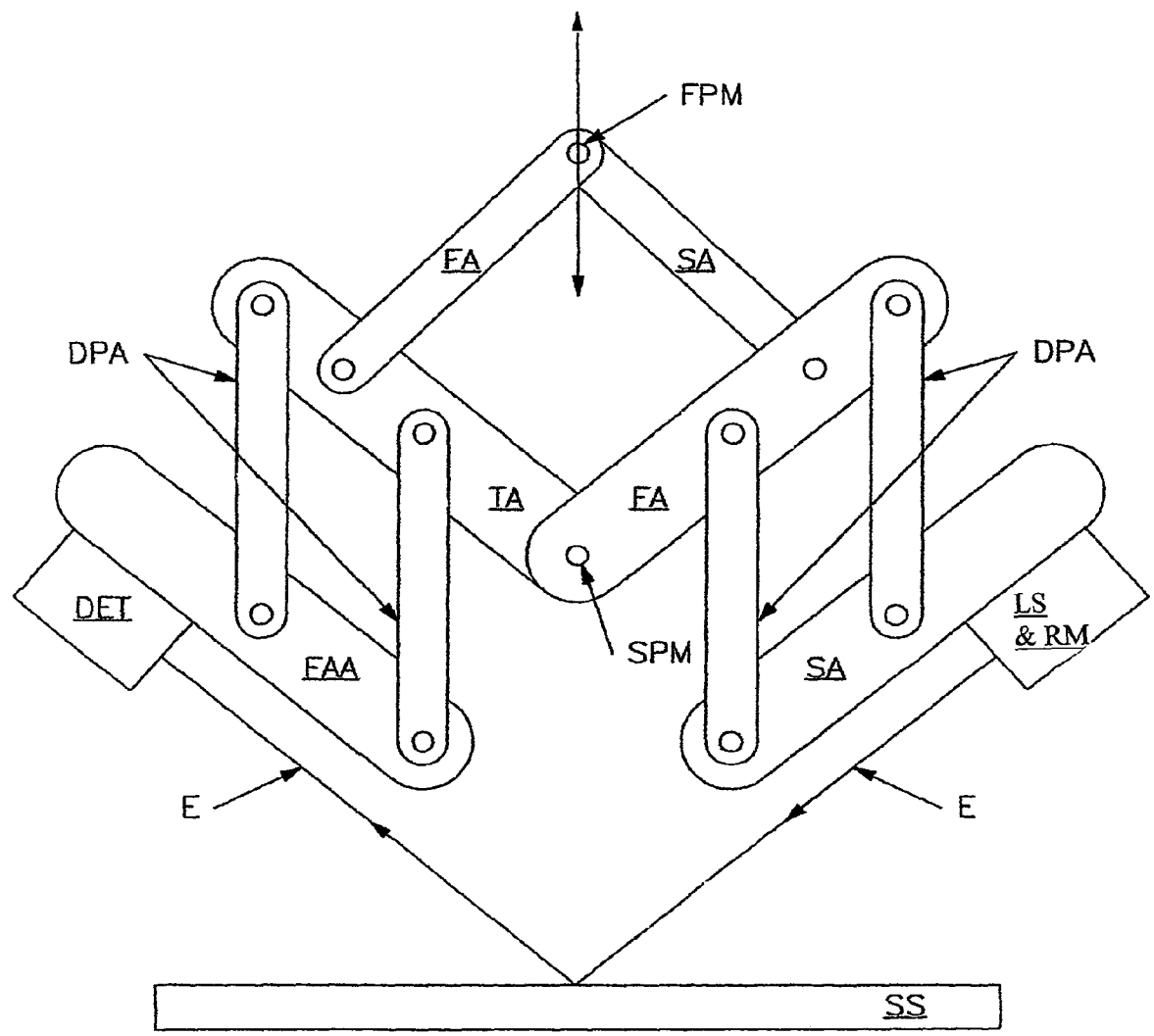
FIG. 4 shows a system, which is presented in patent application Ser. No. 11/105,852, and which allow easily changing the Angle-Of-Incidence of a Beam of Electromagnetic radiation caused to impinge on a Sample.

FIG. 4 shows a system, which is presented in patent application Ser. No. 11/105,852, and which allow easily changing the Angle-Of-Incidence of a Beam of Electromagnetic radiation caused to impinge on a Sample, as well as easily change the vertical height of thereof above the Sample. FIG. 4 shows a mechanical system for mounting an arc-lamp (HAL) and reflective means (RM). Said system for setting the angle of incidence of a beam (E) of electromagnetic radiation comprises, as viewed in elevation, First (FA) and Second (SA) arms pivotally interconnected to one another at an upper aspect thereof by a First Pivot Means (FPM), said first (FA) and second (SA) arms projecting downward and to the left and right of said First Pivot Means (FPM); distal ends of said First (FA) and Second (SA) arms being pivotally affixed to Third (TA) and Forth (FA) arms, said Third (TA) and Forth (FA) arms being pivotally interconnected to one another by Second Pivot Means (SPM) at a lower aspect thereof, said Third (TA) and Forth (FA) arms being projected upward and to the left and right of said Second Pivot Means (SPM) at said lower aspect thereof; there being at least two pivotally affixed substantially Downward Projecting Arms (DPA) to each of said Third (TA) and Forth (FA) arms, distal ends of which are pivotally affixed to Fifth (FAA) and sixth (SA) arms which are not interconnected to one another, but project upward to the left and right, respectively. There are affixed to one of said Fifth (FAA) and Sixth (SA) arms a Source (LS) of a beam of electromagnetic radiation, and to the other of said Sixth (SA) and Fifth (FAA) arms a Detector (DET) of said Beam (E) of electromagnetic radiation. There is further a Sample (SS) located such that a Beam (E) of electromagnetic radiation produced by said Source (LS) of a beam of electromagnetic radiation reflects from an upper surface of said Sample (SS) and enters said detector of said beam of electromagnetic radiation, such that in use when the First Pivot Means (FPM) at which said First (FA) and Second (SA) arms are interconnected is caused to be vertically raised or lowered, the angle of incidence at which the Beam (E) of electric radiation approaches said sample surface is changed, but the location at which it interacts with said Sample (SS) surface remains substantially unchanged.

Figure 5:
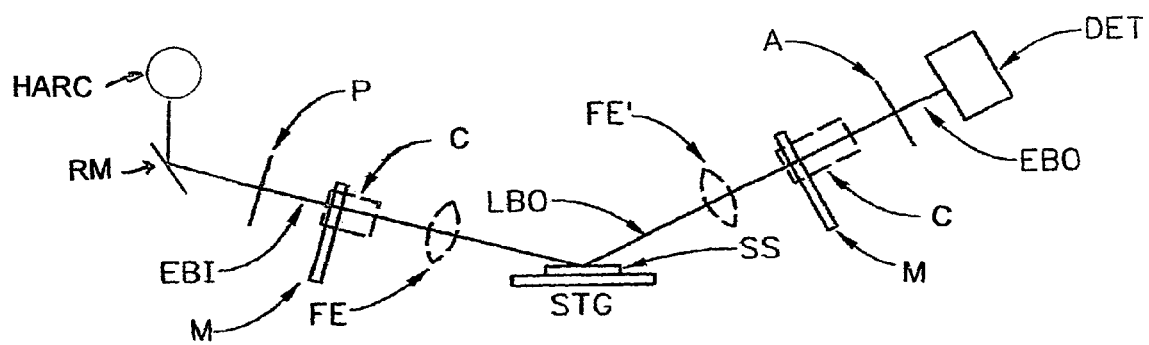
FIG. 5 demonstrates an ellipsometer system.

As a primary application of the above described systems is Ellipsometer, Polarimeter and Mueller Matrix Measuring Systems, FIG. 5 is included for demonstration purposes. Shown are a Horizontally oriented ACR Lamp (HARC), (the longitudinal dimension of which is to be understood as projected into the plane of the paper), and Reflective Means (RM), a Polarizer (P), an optional Compensator (C) and Motor (M) for causing rotation thereof, an optional Focusing Element (FE), a Stage (STG) for supporting a Sample (SS), a second optional Focusing Element (FE), a second optional Compensator (C) and Motor (M) for causing rotation thereof, an Analyzer (A) and a Detector (DET). It is noted that when at least one Compensator (C) is present the system is properly considered a Polarimeter, and when the Polarizer (P), Compensators (C) and Analyzer (A) are removed, the system is a Reflectometer or Spectrophotometer, (which allows a non-polarized beam to transmit through a sample). When two Compensators are present the system can be applied to measure Mueller Matrix elements.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system comprising an arc-lamp which presents with an elongated dimension, said arc-lamp being oriented such that its elongated dimension projects substantially horizontally, said system further comprising means for controlling the vertical location thereof, said system further comprising a reflective means and means for controlling the vertical location thereof and for rotating said reflective means;

such that in use a beam of electromagnetic beam is produced by said arc-lamp and directed out the lower surface thereof onto said reflective means, which reflectively directs it at a first angle-of-incidence onto a spot on a sample surface; and such that when the vertical location of said reflective means is changed and said reflective means is rotated, said beam produced by said arc-lamp and directed out the lower surface thereof onto said reflective means is directed to the same spot on said sample surface at a second angle-of-incidence.

2. A system as in claim 1 in which said the vertical location of said arc-lamp is also changed when the vertical location of said reflective means is changed.

3. A system as in claim 1, which does not require:

necessity of any change in sample orientation, or the necessity of beam directing means other than said reflective means; or the presence of any beam of electromagnetic production means other than said arc-lamp.

\* \* \* \* \*